United States Patent
Yukimasa et al.

(10) Patent No.: US 6,894,511 B2
(45) Date of Patent: May 17, 2005

(54) EXTRACELLULAR RECORDING MULTIPLE ELECTRODE

(75) Inventors: Tetsuo Yukimasa, Hirakata (JP); Hiroaki Oka, Hirakata (JP); Ryuta Ogawa, Moriguchi (JP); Hirokazu Sugihara, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/019,417

(22) PCT Filed: Jul. 12, 2001

(86) PCT No.: PCT/JP01/06067

§ 371 (c)(1),
(2), (4) Date: Dec. 21, 2001

(87) PCT Pub. No.: WO02/06809

PCT Pub. Date: Jan. 24, 2002

(65) Prior Publication Data

US 2002/0113607 A1 Aug. 22, 2002

(30) Foreign Application Priority Data

Jul. 13, 2000 (JP) ........................................ 2000-213531

(51) Int. Cl.[7] ............................................. G01R 27/08
(52) U.S. Cl. ........................ 324/692; 324/691; 324/693
(58) Field of Search ................................ 324/691, 692, 324/693

(56) References Cited

U.S. PATENT DOCUMENTS

| | | | | |
|---|---|---|---|---|
| 5,810,725 A | | 9/1998 | Sugihara et al. | 600/372 |
| 5,981,268 A | * | 11/1999 | Kovacs et al. | 435/287.1 |
| 6,315,940 B1 | * | 11/2001 | Nisch et al. | 435/287.1 |

FOREIGN PATENT DOCUMENTS

| | | |
|---|---|---|
| DE | 198 27 957 A1 | 12/1999 |
| EP | 0 585 933 A2 | 3/1994 |
| EP | 0 689 051 A2 | 12/1995 |
| JP | 4-204244 | 7/1992 |
| JP | 2000-333921 | 12/2000 |
| WO | WO 99/34202 | 7/1999 |

OTHER PUBLICATIONS

"Multichannel Cell Membrane Potential Measuring System and Its Application to Cortical Development Study", by H. Sugihara, et al., National Technical Report vol. 42, No. 2, Apr. 1996, pp. 260–267.

"Immobilization and Culture of the Neurons on the Multi–Electrode Dish", by Kaetsu, et al., Jpn J. Artif Organs 26(3), pp. 767–771 (1997).

"Estimation of Network Structure for Signal Propagations by the Analysis of Multichannel Action Potentials in Cultured Neural Networks", by Konno, et al., pp. 999–1006, 1998.

* cited by examiner

Primary Examiner—Jay Patidar
Assistant Examiner—John Teresinski
(74) Attorney, Agent, or Firm—Snell & Wilmer, LLP

(57) ABSTRACT

A multiple electrode for measuring electro-physiological characteristics of a biological specimen includes a plurality of micro-electrode provided on a first region on a substrate, and a reference electrode provided in a second region on the substrate. The reference electrode includes at least one stimulus reference electrode for applying an electrical signal to the plurality of micro-electrodes. Preferably, the reference electrode includes at least one measurement reference electrode for detecting an electrical signal from the plurality of micro-electrodes, and the stimulus reference electrode is electrically insulated from the measurement reference electrode. Preferably, the second region is placed at a distance from an outer edge of the first region, and surrounds the first region.

9 Claims, 7 Drawing Sheets

EXTRACELLULAR RECORDING MULTIPLE ELECTRODE

TECHNICAL FIELD

The present invention relates to a multiple electrode for extracellular recording, which is useful in the field of electro-physiology and is used in electrical measurement for activities of an organism, particularly to measure changes in potential associated with the activity of neurons.

BACKGROUND ART

Recently, the applicability of neurons to electronic devices has been vigorously studied as well as the medical study. An action potential is generated in a neuron which is in an active state. A change in the ion permeability of a neuron leads to changes in intra- and extracellular ion concentrations which are responsible for generation of an action potential. Therefore, if a potential change in association with a change in ion concentration around a neuron is measured, the activity of the neuron can be monitored.

The above-described action potential associated with the neuron activity is conventionally measured by placing an electrode of glass or metal (e.g., platinum) for measuring an extracellular potential, around a cell with the aid of a micro-manipulator or the like. Alternatively, a similar electrode is inserted into a cell so as to measure the action potential of the cell.

These conventional techniques have the following disadvantages: skill in electrode preparation is required; the electrode has high impedance and therefore the signal is susceptible to external noise; and cells or tissues are injured if an electrode is inserted into the cell. Therefore, conventional electrodes are not suitable for long-term monitoring.

To avoid such problems, the inventors have developed a multiple electrode including a plurality of micro-electrodes made of a conductive material provided on an insulating substrate, and a lead pattern, on which cells or tissue can be cultured (Japanese Laid-Open Publication No. 6-78889, and Japanese Laid-Open Publication No. 6-296595). With this multiple electrode, the activities of neurons can be monitored without injuring cells or tissue for a long period of time. In the above-described multiple electrode, an uppermost surface of the electrode contacting cells is plated with porous platinum black (Japanese Laid-Open Publication No. 6-78889) to adjust the impedance of the electrode to a practical level, i.e., about 50 k$\Omega$ or less.

In the multiple electrode, when measuring the action potentials of neurons, for example, a stimulus (a current or a voltage) is externally applied to a neuron located in a site of a tissue, and the response to the stimulus is monitored at another site, thereby making it possible to analyze a neural network in the tissue. In this case, a micro-electrode, which is located in a site most suitable for application of a stimulus, is selected as a stimulus electrode from a plurality of micro-electrodes on the multiple electrode. Any micro-electrode in the vicinity of the stimulus electrode can be used as a reference electrode. A stimulus is applied between the two micro-electrodes, and response potentials of a plurality of micro-electrodes are measured.

However, other cells or tissues are present on the reference electrode in the vicinity of the stimulus electrode and therefore, if a stimulus (a current or a voltage) is externally applied, not only the cell on the stimulus electrode but also other, cells on the reference electrode are stimulated. Therefore, the desired signal is often not accurately measured. Further, if the impedance of the reference electrode is increased, artifacts due to external noise or stimulus cannot be prevented from being increased.

DISCLOSURE OF THE INVENTION

The present invention is intended to solve the above-described problems. An object of the present invention is to provide a multiple electrode suited to measure an electrical signal of a cell, which is not easily affected by external noise and in which artifacts due to the stimulus are reduced.

The inventors found that when an extracellular recording multiple electrode was produced in such a manner that a reference electrode was placed at a sufficient distance from a stimulus electrode and therefore a cell or tissue is not present on the reference electrode, the electrode is not easily affected by external noise and artifacts due to the stimulus were reduced. Based on this finding, the inventors have completed the present invention.

The inventors also found that the stimulus reference electrode and the measurement reference electrode were electrically separated from each other, whereby the influence of external noise and the artifacts due to the stimulus were further reduced. Based on this finding, the inventors have completed the present invention.

The present invention relates to a multiple electrode for measuring electro-physiological characteristics of a biological specimen. The multiple electrode includes a plurality of micro-electrodes provided on a first region on a substrate, and a reference electrode provided in a second region on the substrate. The reference electrode includes at least one stimulus reference electrode for applying an electrical signal to the plurality of micro-electrodes.

Preferably, the reference electrode includes at least one measurement reference electrode for detecting an electrical signal from the plurality of micro-electrodes, and the stimulus reference electrode is electrically insulated from the measurement reference electrode.

Preferably, the second region is placed at a distance from an outer edge of the first region, and surrounds the first region.

Preferably, the biological specimen is placed in such a manner as to overlap with the first region and not to overlap with the second region.

Preferably, the distance is set to a value such that an electrical signal generated from a micro-electrode receiving an applied electrical signal is detected, and electrical noise generated from a micro-electrode receiving no applied electrical signal is not detected.

Preferably, each reference electrode is placed at a position such that the reference electrode does not overlap with the biological specimen placed on the first region.

Preferably, the distance is 0.1 mm or more, and is more preferably in the range of from 1 mm to 10 mm.

Preferably, each measurement reference electrode is placed at a distance of 1 mm or more, more preferably 5 to 11 mm, from a center of the first region.

Preferably, if there are a plurality of the stimulus reference electrodes or the measurement reference electrodes, these reference electrodes are arranged symmetrically about the center of the first region.

Preferably, the plurality of micro-electrodes are arranged in a matrix within the first region.

Preferably, the multiple electrode includes a wiring portion capable of providing each micro-electrode with an electrical signal or extracting an electrical signal from each micro-electrode.

According to an aspect of the present invention, an integrated cell installer includes the above-described multiple electrode, in which the integrated cell installer has a cell installing region for placing a biological specimen on the substrate of the multiple electrode.

According to another aspect of the present invention, a cellular potential measuring apparatus includes the above-described integrated cell installer, an output signal processor connected to the micro-electrodes for processing an output signal due to an electro-physiological activity of a biological specimen, and a stimulus signal provider for optionally providing an electrical stimulus to the biological specimen.

The present invention also relates to a cellular potential measuring system including the above-described cellular potential measuring apparatus, and an optical monitoring apparatus for optically monitoring a biological specimen; and/or a cell culture apparatus for controlling the culture environment of the biological specimen.

BEST MODE FOR CARRYING OUT THE INVENTION

Figure 1:
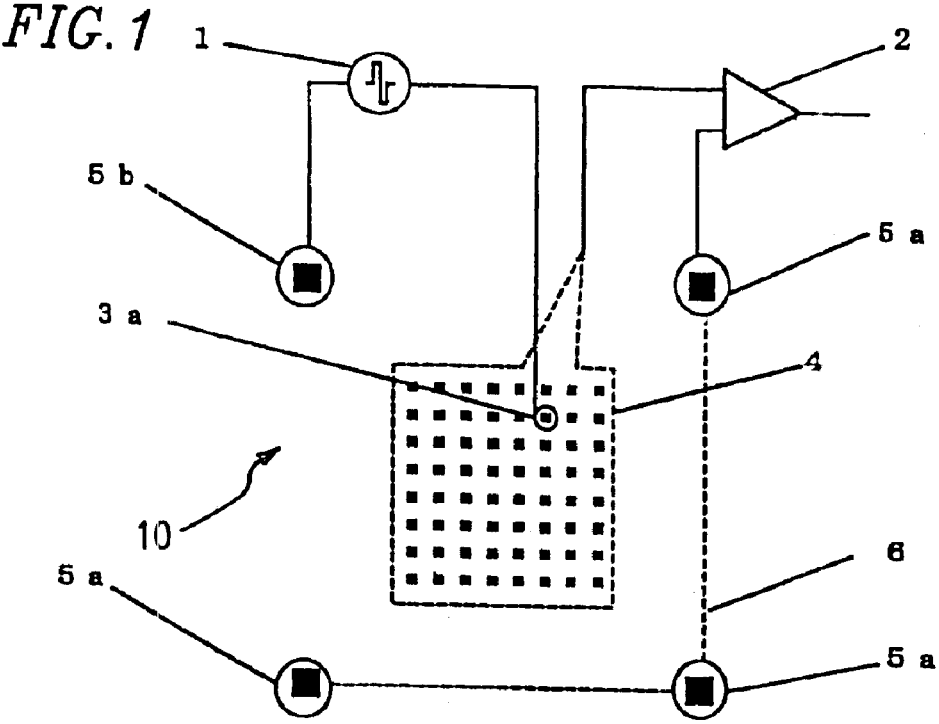
FIG. 1 is a schematic block diagram showing a cellular potential measuring apparatus according to the present invention including a multiple electrode. Reference numerals in the figure indicate the following members: 1 stimulus signal provider; 2 output signal processor; 3a stimulus micro-electrode; 10 multiple electrode; 4 region including micro-electrodes; 5a measurement reference electrode; 5b stimulus reference electrode; and 6 line representing electrical short circuit.

Hereinafter, the present invention will be described in detail.

(Micro-electrode and Reference Electrode)

A multiple electrode according to the present invention includes a plurality of micro-electrodes provided on a first region on an insulating substrate. A biological specimen, such as a cell or tissue, is placed in the first region to measure the electrical activity of a cell in the biological specimen.

The multiple electrode of the present invention is characterized by including at least one reference electrode (stimulus reference electrode) which is different from the plurality of micro-electrodes. The reference electrode is used to stimulate each micro-electrode with an electrical signal.

The multiple electrode of the present invention may further include at least one reference electrode (measurement reference electrode) for detecting an electrical signal from each micro-electrode. The above-described reference electrodes (the stimulus reference electrode and the measurement reference electrode) are provided in a second region on the insulating substrate. Preferably, the reference electrodes are each placed a sufficient distance from the first region including the micro-electrodes. Preferably, the stimulus reference electrode and the measurement reference electrode are electrically separated from each other.

In the multiple electrode of the present invention, representatively, the plurality of micro-electrodes are provided in the first region on the substrate in such a manner as to be placed at intersections of a grating in the form of a matrix. In this arrangement, the plurality of electrodes can be equally spaced. Therefore, adjacent neurons in a biological specimen can be placed on adjacent electrodes to detect transfer of an electrical signal between the adjacent cells.

In the multiple electrode of the present invention, representatively, the plurality of reference electrodes are arranged in the second region in such a manner as to be symmetrical with respect to the center of the first region. Therefore, detection of electrical noise from the micro-electrodes due to the stimulus can be reduced.

Each micro-electrode is externally provided with an electrical signal. Alternatively, a wiring portion for extracting an electrical signal from each micro-electrode to the outside is connected to each electrode. Representatively, the wiring portion includes a lead line which is connected to each micro-electrode and drawn from the electrode towards the periphery of the substrate. The wiring portion may further include an electrical junction connected to an end of the lead line which is typically located at the periphery of the substrate. An example of a material for the wiring portion preferably includes indium tin oxide (ITO).

Representatively, the surface of a lead line is covered with an insulating layer. The insulating layer may be provided only on the lead line, but preferably on almost the entire upper surface of the substrate except for the micro-electrodes and the vicinity of the electrical junctions. Examples of the insulating layer preferably include acrylic resin or photosensitive polyimide which are easy to process.

(Configuration of Multiple Electrode)

For the detailed design of the multiple electrode of the present invention, any structural features of a known multiple electrode (e.g., Japanese Laid-Open Publication No. 6-78889) can be used as long as the provision of the stimulus reference electrode is not interfered with. Hereinafter, a representative example of a configuration of the multiple electrode will be shown. Embodiments as described herein may be optionally modified by taking into consideration various factors, such as the characteristics of the biological specimen to be measured, the nature of data to be measured, and the like.

The substrate included in the multiple electrode is preferably made of a transparent insulating material for the purpose of optical monitoring after cell culture. Examples of such a material include: glass, such as silica glass, flint glass, and borosilicate glass; an inorganic substance, such as quartz; polymethylmethacrylate or a copolymer; and a transparent organic substance, such as polystyrene, and polyethylene terephthalate. An inorganic substance which has mechanical strength and transparency is preferable.

Examples of a material for the electrodes provided on the substrate include indium tin oxide (ITO), tin oxide, Cr, Au, Cu, Ni, Al, and Pt. Among other things, ITO and tin oxide are preferable. ITO having transparency and a high level of conductivity is particularly preferable. The above-described micro-electrode is typically produced by providing the porous conductive material plating on the uppermost surface of a part of the electrode material having a desired position and shape.

Typically, a plurality of micro-electrodes are equally spaced in such a manner that the distances between adjacent electrodes are all equal to each other. The distances between adjacent electrodes may be representatively in the range of from about 10 to about 1000 $\mu$m. Representatively, the shape of the electrode is substantially a square or a circle with an edge or a diameter within the range of from about 20 to about 200 $\mu$m. With the above-described settings, if a biological specimen to be measured, e.g., the cell body of a neuron (i.e., a cell body, a dendrite, and an axon) is located on a micro-electrode, it is highly probable that another cell body, to which a dendrite of the former cell body is connected, is located on an adjacent electrode.

Typically, a plurality of reference electrodes are also equally spaced in such a manner that distances between most adjacent reference electrodes are equal to each other. The distance between the most adjacent reference electrodes may be representatively in the range of from about 8 mm to about 16 mm. Representatively, the shape of the electrodes is substantially a square or a circle with an edge or a diameter within the range of from about 80 $\mu$m to about 800 $\mu$m. With the above-described settings, detection of electrical noise generated from the micro-electrode can be reduced.

In the multiple electrode of the present invention, the second region is typically provided at a distance of about 0.1 mm or more from the periphery of the first region. Theoretically, the greater the distance, the lesser the probability that the reference electrode detects noise. The upper limit of the distance is defined mainly by a structural feature of the multiple electrode. In a representative multiple electrode, the reference electrode is provided within an internal diameter of a ring defining a cell installing region described later (representatively, about 22 mm$\phi$). Therefore, typically, the distance does not exceed about 10 mm and is representatively within the range of from about 1 mm to about 10 mm.

When the second region is provided at a distance of about 0.1 mm or less from the periphery of the first region, crosstalk occurs between the reference electrode and the adjacent micro-electrode due to the influence of biological specimens which overlap with the first region.

Figure 9:
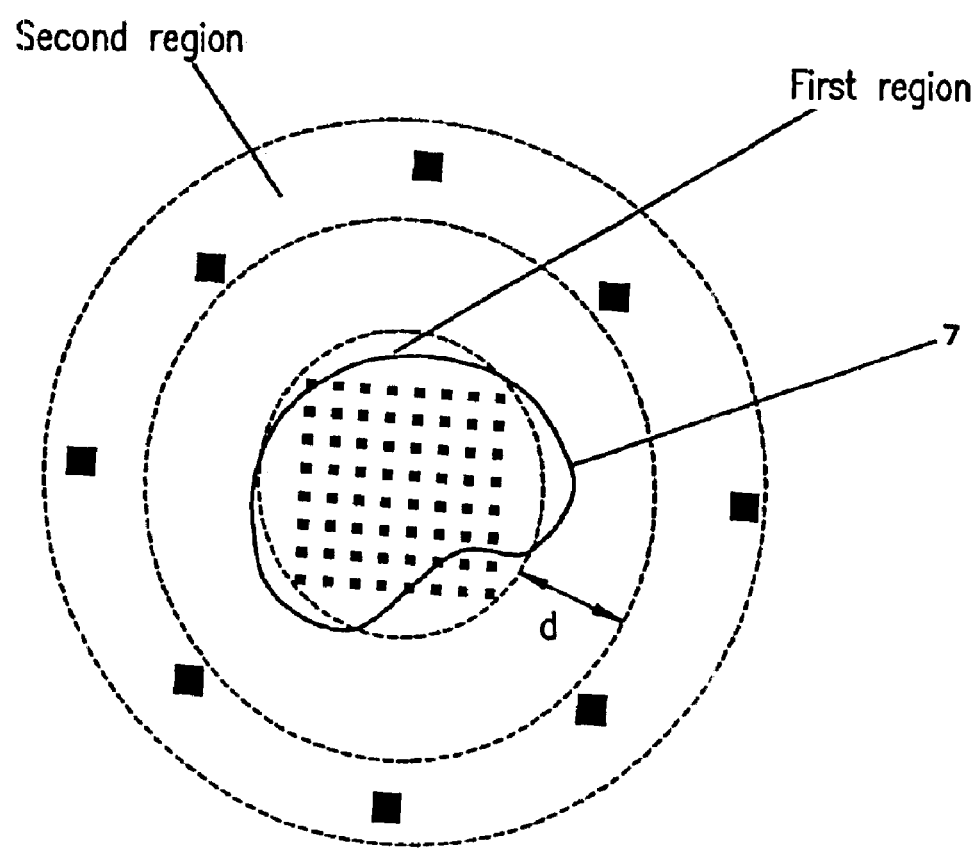
FIG. 9 is a conceptual diagram showing a relationship between a first region in which micro-electrodes are provided and a second region in which reference electrodes are provided.

FIG. 9 is a conceptual diagram showing a relationship between the first region and the second region. In FIG. 9, there are three concentric circles indicated by dashed lines. The region enclosed by the innermost circle is the first region including the micro-electrodes (represented by small black squares in the figure). The doughnut-like region interposed by the middle circle and the outermost circle is the second region including the reference electrodes (represented by small black squares in the figure). Letter d indicates the distance between an outer edge of the first region and the second region.

The lead line connected to the micro-electrode may be made of the same electrode material as those described. In this case, ITO is also preferable. Typically, such an electrode material is deposited on a substrate. Thereafter, etching is conducted using a photoresist, thereby forming a desired integrated pattern of a lowermost layer of the micro-electrode and a wiring portion including a lead line. In this case, the thicknesses of the lowermost layer of the micro-electrode and the wiring portion may be about 500 to 5000 angstroms.

The lead line is representatively arranged extending substantially radially from each micro-electrode. In combination with this substantially radial arrangement, a plurality of micro-electrodes are particularly preferably arranged in such a manner that the centers thereof are placed on respective intersections of an 8×8 grating.

An example of a material for an insulating layer covering the lead line includes a transparent resin, such as a polyimide (PI) resin and an epoxy resin. A photosensitive resin, such as negative photosensitive polyimide (NPI), is preferable. For example, when a photosensitive resin is used as the insulating layer material, it is possible to expose only the electrode by forming an opening in the insulating layer portion on the micro-electrode by utilizing a pattern formed by photoetching. As described above, the insulating layer is provided in such a manner as to cover substantially the entire surface of the insulating substrate except for the vicinity of the electrodes and the electrical junctions with external circuits. This is preferable in terms of production efficiency and the like.

(Apparatus and System for Measuring Cellular Potential)

For the detailed design of various components of a system for effectively utilizing the multiple electrode of the present invention for measuring neurons or the like, any structural features of a known multiple electrode (see, e.g., Japanese Laid-Open Publication No. 8-62209) can be adopted.

Typically, the multiple electrode of the present invention is additionally provided with a structure for facilitating cell culture to be conducted on the multiple electrode and optionally with another structure for facilitating handling of the multiple electrode. The resultant multiple electrode may be provided as an integrated cell installer.

In order to conduct cell culture on the multiple electrode, representatively, a structural member capable of holding culture medium may be provided via the insulating layer on the substrate which is substantially entirely covered with the insulating layer. For example, a cylinder-like frame made of polystyrene may be fixed on the substrate in such a manner as to surround the first region including a plurality of micro-electrodes and the second region including reference electrodes. In this case, the inside of the polystyrene frame defines a cell holding region.

In order to facilitate the handling of the multiple electrode in measuring cells, for example, a printed circuit board may be used. The printed circuit board has a conductor pattern conductively connected to electrical junctions on the multiple electrode, thereby playing a role in extending an electrical connection, which is established from the micro-electrode to the electrical junction, to the outside. A holder having an appropriate shape, such as a two-part split holder which sandwiches the multiple electrode, may be used to reliably fix the printed circuit board with the multiple electrode while keeping the electrical connection therebetween, for example.

The integrated cell installer may be further combined with a stimulus signal provider and an output signal processor, thereby obtaining a cellular potential measuring apparatus for electrically stimulating cells on the multiple electrode, and processing an output signal which is the response to the stimulus.

The stimulus signal provider can apply a stimulus signal to any micro-electrode out of the plurality of micro-electrodes and any stimulus reference electrode. When a cell responds to the stimulus signal, another electrode detects a change in evoked potential and outputs an output signal corresponding to the change to a signal processor. The output signal is transferred via an appropriate process to a display apparatus or the like, for example. Note that a spontaneous potential generated in a cell without receiving a stimulus signal may be simultaneously measured.

The stimulus signal provider and the output signal processor are representatively realized by a single computer having appropriate measurement software. The measurement software provides, on a computer screen, a parameter setting window for setting stimulus conditions and the like, a recording window for recording a potential change detected from a cell and displaying the data via multiple channels in real time, a data analyzing window for analyzing recorded data, and the like. Preferably, a stimulus signal from a computer is transferred via a D/A converter to the multiple electrode, while an output signal from a cell is transferred via an A/D converter to a computer.

A cellular potential measuring apparatus may be further combined with an optical monitoring apparatus and a cell culture apparatus, thereby obtaining a cellular potential measuring system for culturing neurons for a long period of time, and stably and accurately measuring the electrophysiological activities of the neurons. The optical monitoring apparatus may include an inverted microscope, and further an SIT camera for a microscope including a high-definition display and an image file apparatus.

As the cell culture apparatus, any apparatus or combination thereof which can control the temperature of the culture atmosphere, the circulation of culture medium, the supply of a gas mixture of air and carbon dioxide, and the like, can be used.

The multiple electrode, integrated cell installer, cellular potential measuring apparatus, or cellular potential measuring system of the present invention is used to analyze a neural network or the like, in which, for example, a stimulus (a current or a voltage) is applied to a specimen (i.e., a neuron), and an electrical signal pattern obtained as a response to the stimulus is monitored. If electrical signal patterns are obtained in the presence or absence of predetermined compounds and compared with each other, the compounds can be screened for their activity on a specimen.

Further, for example, an electrical signal pattern may be obtained in the presence of a compound which is known to act on a neuron. Therefore, a database on electrical signal patterns relating to the effects of nerve agents can be constructed.

If such a database is constructed, the mode of action of a compound having an unknown action on a neuron can be deduced by comparing an electrical signal pattern obtained in the presence of the compound with the database to identify a known compound which has an action on a neuron similar to that of that compound.

Therefore, the multiple electrode, integrated cell installer, cellular potential measuring apparatus, or cellular potential measuring system of the present invention may be used as a drug screening apparatus.

EXAMPLES

Hereinafter, the present invention will be specifically described by way of illustrative examples. The present invention is not limited to these examples.

Example 1

FIG. 1 is a schematic block diagram showing a cellular potential measuring apparatus for measuring electrophysiological characteristics of a cell, including a multiple electrode according to the present invention. For comparison, a cellular potential measuring apparatus including a conventional multiple electrode is shown in a schematic block diagram in FIG. 2.

The multiple electrode (10) of the present invention includes: 64 micro-electrodes (3a) arranged in the form of a matrix within a substantially square-like region enclosed by a dashed line 4 (each micro-electrode has a size of 50×50 $\mu$m and a central portion thereof is placed at a corresponding intersection of an 8×8 grating; and 4 reference electrodes (5a: measurement reference electrodes and 5b: stimulus reference electrodes) (each reference electrode has a size of 200 $\mu$m×200 $\mu$m and a central portion of each reference electrode is placed at a corresponding vertex of a square having a side length of about 8.5 mm. In this case, a distance between the first region and the second region is about 5 mm). The multiple electrode (10) is connected to a stimulus signal provider 1 and a cellular potential measuring apparatus 2. The stimulus reference electrode (5b) and the measurement reference electrode (5a) each have a surface area of about 0.04 mm$^2$. The stimulus reference electrode (5b) is electrically separated from the measurement reference electrode (5a). Note that in FIGS. 1, 2, 5 and 6, a dashed line between each measurement reference electrode and a dash-dot line between each stimulus reference electrode indicate electrical short circuits which are typically established by an electrical circuit in an amplifier.

Initially, the apparatus shown in FIG. 1 was used without any specimen being placed on the electrode. A 10 $\mu$A constant current having a bipolar pulse (where the pulse width is 100 $\mu$sec) was applied as a stimulus to a micro-electrode positioned at the second row and the sixth column. In this situation, the noise level of each micro-electrode was measured and the influence of artifacts was studied. Noise level measurement was conducted by displaying evoked potential responses on a computer screen having 64 channels corresponding to the respective micro-electrodes. Note that each micro-electrode was connected via a lead line on the substrate and an A/D converter to a computer.

Responses of the 64 micro-electrodes were monitored from 5 msec before stimulation of the constant current bipolar pulse to 20 msec after the stimulation. The results are shown in FIG. 3.

Figure 2:
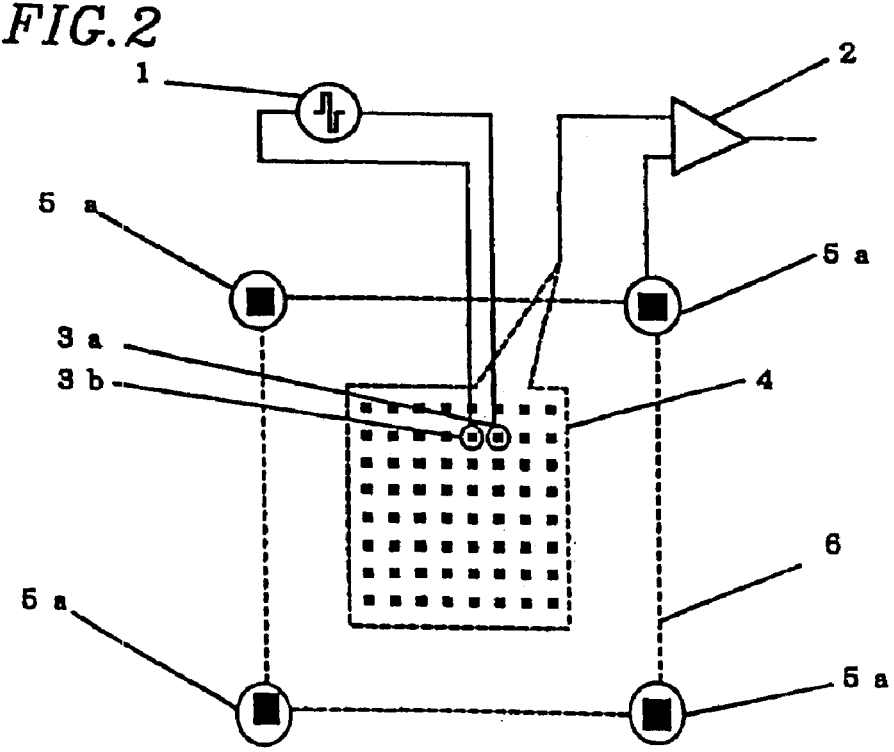
FIG. 2 As a schematic block diagram showing a cellular potential measuring apparatus including a conventional multiple electrode. Reference numerals in the figure indicate the same members as those in FIG. 1, except for 3b indicating a stimulus reference micro-electrode.

For a control, an apparatus including a conventional multiple electrode shown in FIG. 2 was used. A 10 µA constant current having a bipolar pulse similar to that described above was applied between a pair of micro-electrodes including a micro-electrode positioned at the second row and the sixth column as shown in FIG. 2. 64 channels were monitored. The results are shown in FIG. 4.

Figure 4:
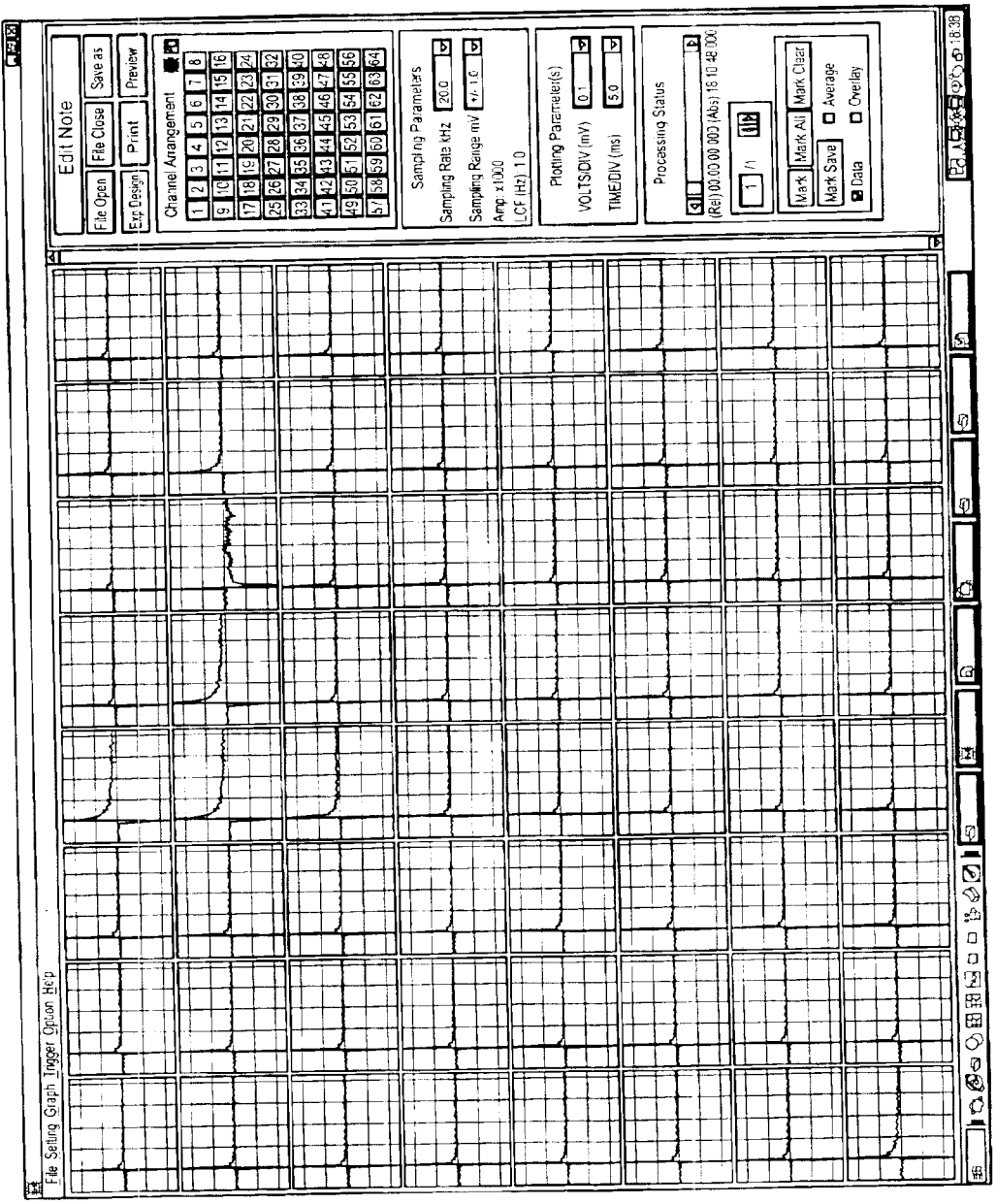
FIG. 4 is a diagram showing a printout of a computer screen displaying, on 64 channels, noise levels and artifacts a cellular potential measuring apparatus including a conventional multiple electrode with respect to bipolar stimuli of a constant current.

As shown in FIG. 4, in the control apparatus, the micro-electrode positioned at the second row and the sixth column which was used as a stimulus electrode had a considerably high level of noise with a sawtooth waveform. Further, micro-electrodes in the vicinity of the stimulus micro-electrode had significant artifacts. It took 5 to 20 msec for the potential to return to a normal level.

Figure 3:
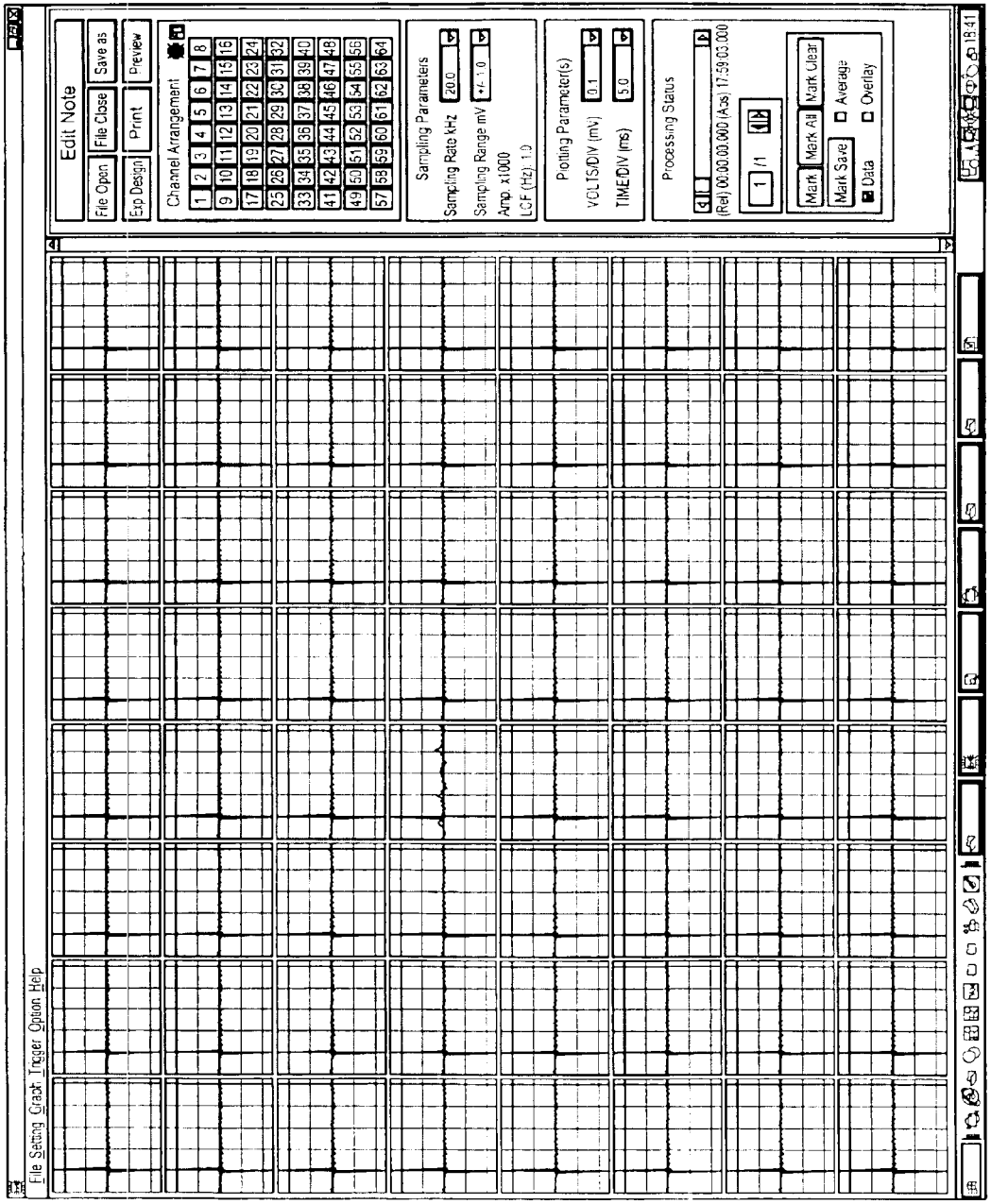
FIG. 3 is a diagram showing a printout of a computer screen displaying, on 64 channels, noise levels and artifacts of a cellular potential measuring apparatus including a multiple electrode according to the present invention with respect to bipolar stimuli of a constant current.

In contrast, in the apparatus including the multiple electrode of the present invention, substantially no noise was detected at the micro-electrode positioned at the second row and the sixth column of the matrix as shown in FIG. 3. Micro-electrodes in the vicinity of the stimulus electrode had considerably small artifacts.

Example 2

The multiple electrode of the present invention shown in FIG. 1 was used. In addition, a cellular potential measuring apparatus including the multiple electrode shown in FIG. 5 including four stimulus reference electrodes was produced. An evoked potential of each micro-electrode was actually measured using a hippocampus slice (brain) of a rat.

Figure 5:
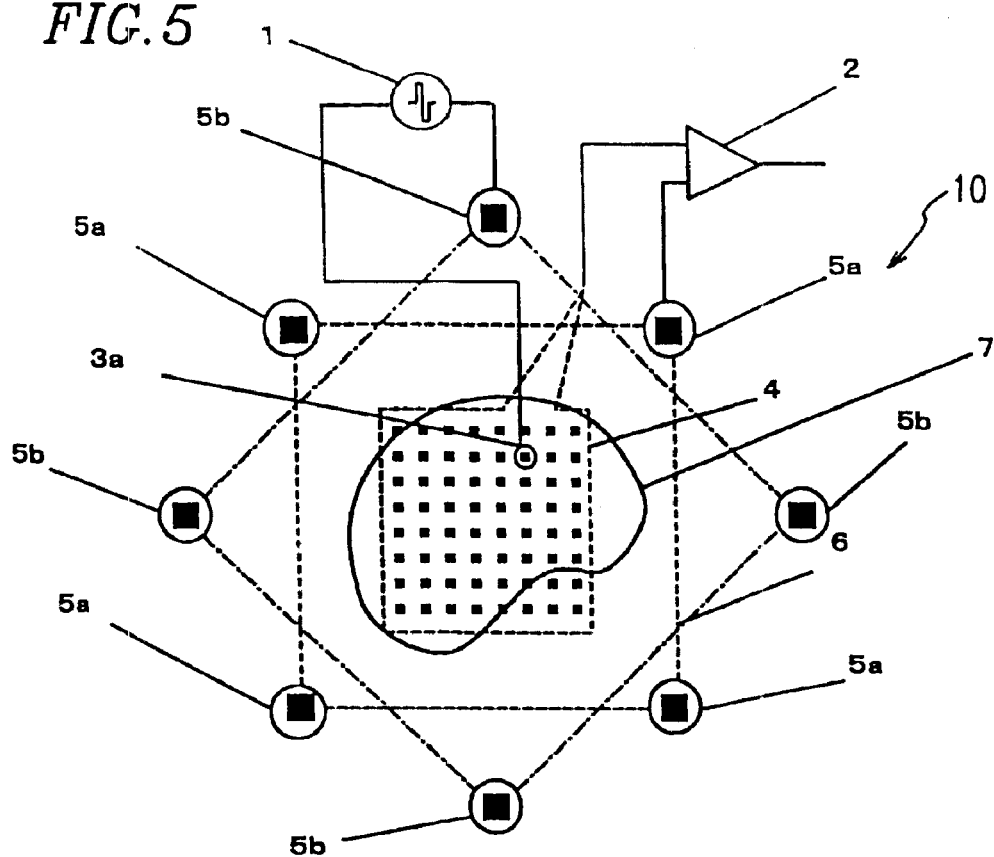
FIG. 5 is a schematic block diagram showing a variation of a cellular potential measuring apparatus including a multiple electrode according to the present invention. Reference numerals in the figure indicate the same members as those in FIG. 1. In addition, reference numeral 7 indicates cells to be measured, and reference numeral 10 indicates the multiple electrode.
Figure 6:
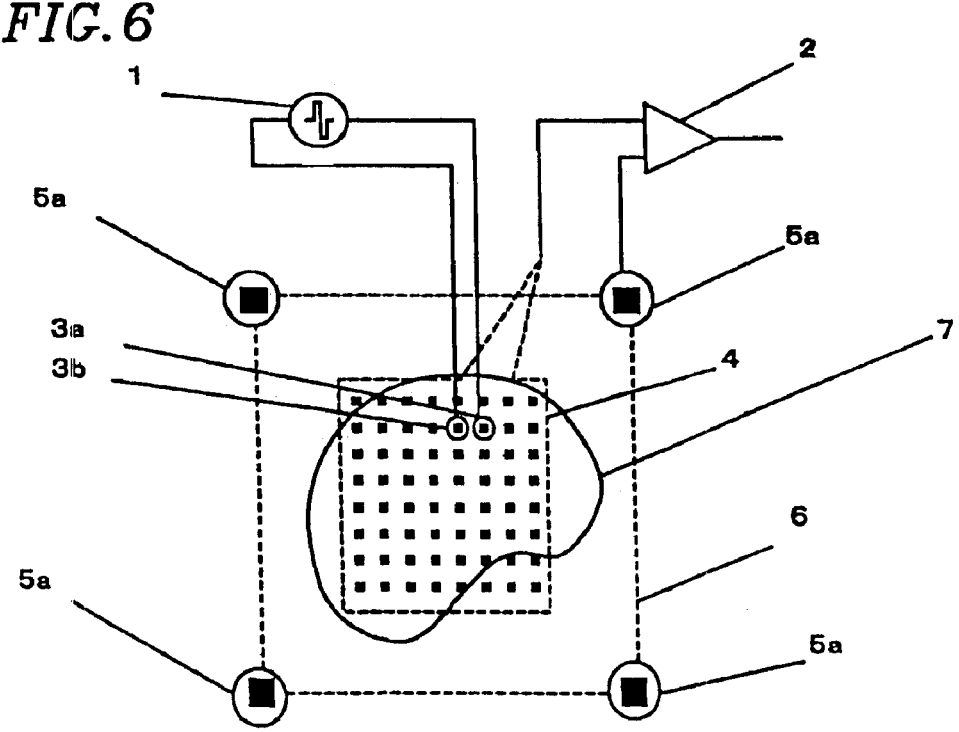
FIG. 6 is a schematic block diagram showing a cellular potential measuring apparatus including a conventional multiple electrode. Reference numerals in the figure indicate the same members as those in FIG. 2 or 5.

In the apparatus shown in FIG. 5, the four stimulus reference electrodes were placed at the vertexes of substantially a square having a side of 8.5 mm. The other features of the apparatus are the same as those of the apparatus shown in FIG. 1. With this apparatus, an evoked potential of each micro-electrode was actually measured using a hippocampus slice (brain) of a rat. FIG. 5 is a schematic block diagram showing a state where a hippocampus slice 7 of a rat was placed on the apparatus.

A four-week-old SD/slc rat was anesthetized with Fluothane and decapitated to remove a whole brain. The removed brain was immediately cooled in Ringer's solution on ice. A brain block containing only the hippocampus was dissected. Thereafter, the obtained brain block was cut by a tissue slicer to give a slice having a thickness of 300 µm. The slice was placed and tested on the micro-electrodes.

Figure 7:
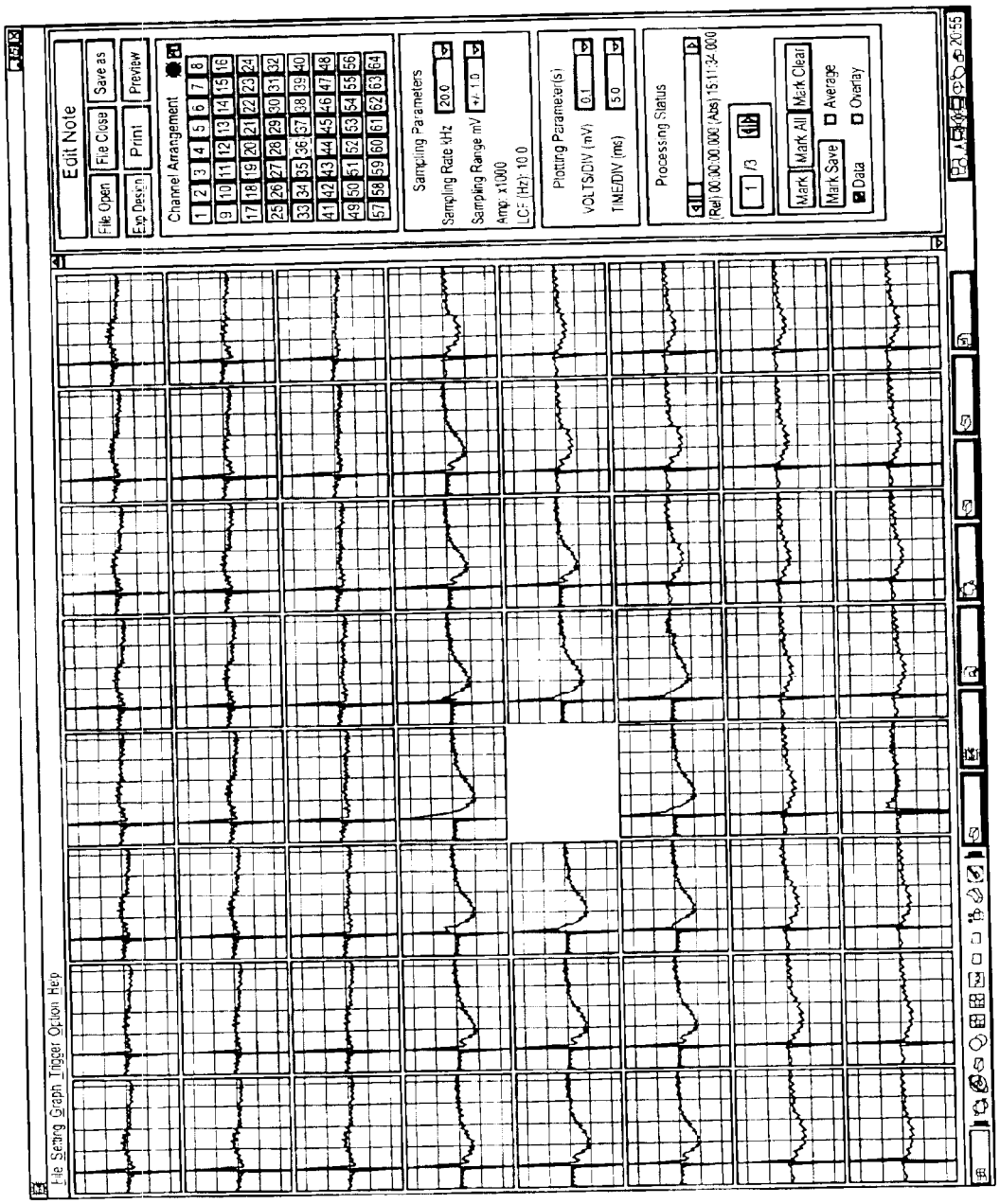
FIG. 7 is a diagram showing a printout of a computer screen 3 is playing, on 64 channels, noise levels and artifacts of a cellular potential measuring apparatus including a variation of a multiple electrode according to the present invention with respect to current stimuli.

Similar to Example 1, evoked potentials were measured in the presence of an applied constant current of 10 µA having bipolar pulses (where a pulse width is 100 µsec). The stimulus was applied to a micro-electrode positioned at the second row and the second column in the matrix in the apparatus shown in FIG. 1, and to a micro-electrode positioned at the second row and the sixth column in the matrix in the apparatus shown in FIG. 5. The measurement results are shown on a computer screen as shown in FIG. 7. FIG. 7 shows the results when the apparatus shown in FIG. 5 was used. For a control, an apparatus including the conventional multiple electrodes shown in FIG. 6 was used. A 10 µA constant current having bipolar pulses similar to that described above was applied to a pair of micro-electrodes including the micro-electrode positioned at the second row and the sixth column shown in FIG. 6, and a similar test was conducted. The results are shown in FIG. 8.

Figure 8:
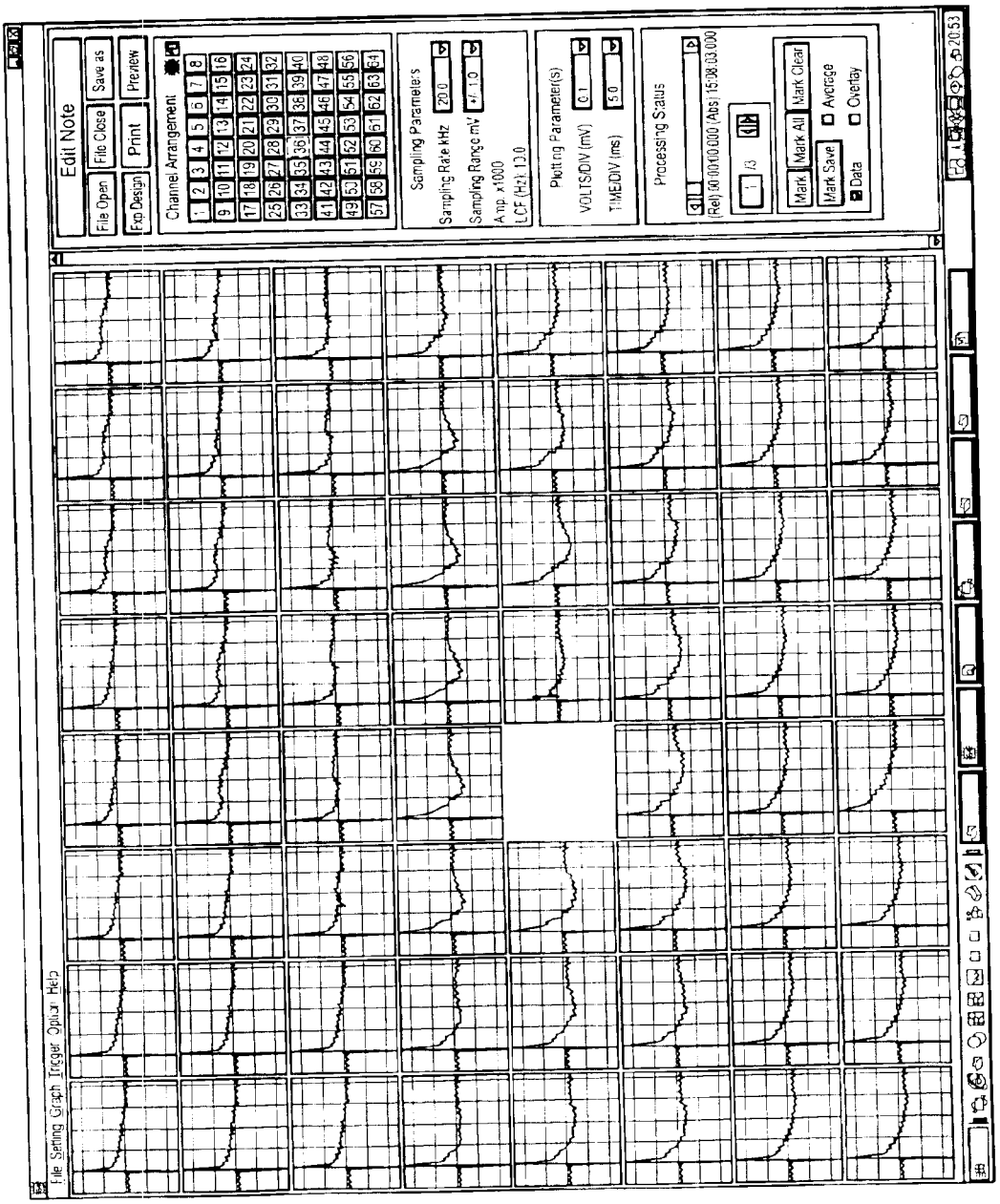
FIG. 8 is a diagram showing a printout of a computer screen displaying, on 64 channels, noise levels and artifacts of a cellular potential measuring apparatus including a conventional multiple electrode with respect to current stimuli.

As shown in FIG. 8, on almost all channels of the conventional multiple electrode, it took 20 msec for electrical signals of neurons, represented by a wave which is below a baseline and has a minimum point, to return to the normal potential (20 msec corresponds to 4 units or more in the channels shown in FIG. 8). In contrast, in the apparatus including the multiple electrode of the present invention shown in FIG. 7, on all of the channels, electrical signals from all cells returned to a normal potential within 20 msec. In the apparatus including the multiple electrode of the present invention shown in FIG. 1, on all of the channels, electrical signals from all cells also returned to a normal potential within 20 msec. As described above, the apparatuses including the multiple electrode of the present invention have a low noise level and are less affected by artifacts, whereby evoked potentials could be satisfactorily measured.

Although the present invention is described with reference to the above-described examples, the present invention is not limited to these examples. The present invention may be implemented to modified, improved, and changed embodiments based on knowledge of those skilled in the art without departing the scope of the present invention.

INDUSTRIAL APPLICABILITY

A multiple electrode suited to record an electrical signal of a cell is provided, which is not easily affected by external noise and in which artifacts due to the stimulus is reduced.

What is claimed is:

1. A multiple electrode for measuring electrophysiological characteristics of a biological specimen, comprising:

a substrate;

a plurality of micro-electrodes provided on the substrate; and a reference electrode provided on the substrate, wherein on the substrate, there is a first region for placing the biological specimen and a second region which is away from the first region, wherein the plurality of micro-electrodes are located in the first region and the plurality of micro-electrodes include at least one measurement electrode and at least one stimulus electrode, and the reference electrode is located in the second region, and the reference electrode includes at least one measurement reference electrode and at least one stimulus reference electrode which is different from the at least one measurement reference electrode.

2. A multiple electrode according to claim 1, wherein the at least one measurement reference electrode detects an electrical signal from the plurality of micro-electrodes, and the at least one stimulus reference electrode is electrically insulated from the at least one measurement reference electrode.

3. A multiple electrode according to claim 1, wherein the second region is placed at a distance from an outer edge of the first region, and surrounds the first region.

4. A multiple electrode according to claim 3, wherein the distance is set to a value such that an electrical signal generated from a micro-electrode receiving an applied electrical signal is detected, and electrical noise generated from a micro-electrode receiving no applied electrical signal is not detected.

5. A multiple electrode according to claim 2, including a plurality of stimulus reference electrodes and a plurality of measurement reference electrodes, and the plurality of stimulus reference electrodes or the plurality of measurement reference electrodes are substantially symmetrically provided with respect to a center of the first region.

6. A multiple electrode according to claim 1, wherein the plurality of micro-electrodes are arranged in a matrix within the first region.

7. An integrated cell installer comprising a multiple electrode according to claim 1, wherein the integrated cell installer has a cell installing region for placing a biological specimen on the substrate of the multiple electrode.

8. A cellular potential measuring apparatus comprising: an integrated cell installer according to claim 7; an output signal processor connected to the micro-electrodes for processing an output signal due to an electro-physiological activity of a biological specimen; and a stimulus signal provider for optionally providing an electrical stimulus to the biological specimen.

9. A cellular potential measuring system comprising: a cellular potential measuring apparatus according to claim 8; and an optical monitoring apparatus for optically monitoring a biological specimen; and/or a cell culture apparatus for controlling the culture environment of the biological specimen.

* * * * *